US008114835B2

(12) United States Patent
Mata et al.

(10) Patent No.: US 8,114,835 B2
(45) Date of Patent: Feb. 14, 2012

(54) SELF-ASSEMBLING PEPTIDE AMPHIPHILES FOR TISSUE ENGINEERING

(75) Inventors: Alvaro Mata, Barcelona (ES); Samuel I. Stupp, Chicago, IL (US)

(73) Assignee: Northwestern University, Evanston, IL (US)

( * ) Notice: Subject to any disclaimer, the term of this patent is extended or adjusted under 35 U.S.C. 154(b) by 304 days.

(21) Appl. No.: 11/937,171

(22) Filed: Nov. 8, 2007

(65) Prior Publication Data

US 2008/0248569 A1 Oct. 9, 2008

Related U.S. Application Data

(60) Provisional application No. 60/857,932, filed on Nov. 9, 2006.

(51) Int. Cl.
  *A61K 38/00* (2006.01)
  *A61P 31/04* (2006.01)
  *A61P 43/00* (2006.01)

(52) U.S. Cl. ..................... 514/3.2; 514/16.5

(58) Field of Classification Search .............. None
See application file for complete search history.

(56) References Cited

U.S. PATENT DOCUMENTS

| | | | |
|---|---|---|---|
| 5,512,294 A * | 4/1996 | Li et al. ............... | 424/450 |
| 6,306,598 B1 | 10/2001 | Charych | |
| 6,875,744 B2 * | 4/2005 | Owen ................ | 514/16 |
| 6,890,654 B2 * | 5/2005 | Stupp et al. ............ | 428/403 |
| 7,030,167 B2 | 4/2006 | Gunther | |
| 7,129,208 B2 | 10/2006 | Gokel et al. | |
| 7,371,719 B2 | 5/2008 | Stupp et al. | |
| 2006/0110437 A1 | 5/2006 | Stupp et al. | |
| 2006/0159837 A1 | 7/2006 | Kaplan et al. | |
| 2008/0175883 A1 * | 7/2008 | Hsu et al. ............. | 424/423 |

OTHER PUBLICATIONS

Hartgerink et al. Peptide-amphiphile nanofibers: A versatile scaffold for the preparation of self-assembling materials. PNAS. Apr. 16, 2002, vol. 99, No. 8, pp. 5133-5138.*
Biesalski et al. Polymerized Vesicles Containing Molecular Recgnition Sites. Langmuir. 2005, vol. 21, pp. 5663-5666.*
Reichel et al. Synthesis and Supramolecular Characterization of a Novel Class of Glycopyranosyl-Containing Amphiphiles. J. Org. Chem. 2000. vol. 65, pp. 3357-3366.*
Beniash et al., "Self-assembling peptide amphiphile nanofiber matrices for cell entrapment" 2005 Acta Bio. 1:387-97.
Biesalski et al, "Cell adhesion on a polymerized peptide-amphiphile monolayer" 2006, Biomaterials 27:1259-1269.
Bull et al. "Self-assembled peptide amphiphile nanofibers conjugated to MRI contrast agents" 2005 Nano Lett. 5:1-4.
Curtis and Wilkinson "Topographical control of cells" 1998 Biomaterials 18:1573-1583.
Hartgerink et al., "Peptide-Amphiphile Nanofibers: A Versatile Scaffold for the Preparation of Self-Assembling Materials." PNAS 2002 vol. 99 No. 8 pp. 5133-5138.
Hosseinkhani et al., "Design of Tissue-engineered Nanoscaffold Through Self-assembly of Peptide Amphiphile" 2006, T. Bio. Comp. Poly. 21:277.
Jahnke et al. "Topochemical polymerization in supramolecular polymers of oligopeptide-functionalized diacetylenes." 2006, Angew. Chem. 45:5383.
Lee et al. "Surface dispersion and hardening of self-assembled diacetylene nanotubes." 2005, Nano Lett. 5:2202-6.
Mata et al. "Analysis of Connective Tissue Progenitor Cell Behavior on Polydimethylsiloxane Smooth and Channel Micro-Textures" 2002 Biomed. Microdev. 4:267-275.
Mata et al. "Growth of connective progenitor cells on microtextured polydimethylsiloxane surfaces" 2002, J. Biomed. Mat Res. 62:499-506.
Nezu and Lando, "Polymerization and Characterization of Polyfunctional Amphiphilic Diacetylenes" 1995, 33:2455.
Niece et al., "Self-assembly combining two bioactive peptide-amphiphile molecules into nanofibers by electrostatic attraction" 2003, J. Am. Chem. Soc. 125:7146-7.
Reichel et al. "Synthesis and Supramolecular Characterization of a Novel Class of Glycopyranosyl-Containing Amphiphiles." J. Org. Chem. 2000 vol. 65 pp. 3357-3366.
Silva et al., "Selective differentiation of neural progenitor cells by high-epitope density nanofibers" 2004, Science 303:1352-5.
Stendahl et al., "Intermolecular Forces in the Self-Assembly of Peptide Amphiphile Nanofibers" 2006, Adv. Func. Mat 16:499.
Uemura T. et al. "Topotactic linear radical polymerization of divinylbenzenes in porous coordination polymers." Angew Chem Int Ed Engl. 2007;46(26):4987-90.
von Recum et al. "Surface roughness, porosity, and texture as modifiers of cellular adhesion" 1996, Tissue Eng. 2:241-253.
Xia and Whitesides "Soft lithography" 1998, Ann. Rev. Mat. Sci. 28:153-184.

* cited by examiner

*Primary Examiner* — Marcela M Cordero Garcia
(74) *Attorney, Agent, or Firm* — Casimir Jones, S.C.

(57) ABSTRACT

The present invention provides for compositions and methods for creating self-assembled peptide amphiphile (PA) structures. In particular, the present invention provides for two and three-dimensional structures of crosslinked PA microtexture structures useful for tissue engineering and drug discovery.

13 Claims, 12 Drawing Sheets

(a) Cells on PA CHANNELS (b) Cells on PA HOLES

KKLLA(K)-(COC$_8$H$_{16}$)
        -diacetylene-(C$_{12}$H$_{25}$)

(a2)

RGDSKKLLA(K)-(COC$_8$H$_{16}$)
        -diacetylene-(C$_{12}$H$_{25}$)

(b)

```
SEQUENCE LISTING

<160> NUMBER OF SEQ ID NOS: 3

<210> SEQ ID NO 1
<211> LENGTH: 7
<212> TYPE: PRT
<213> ORGANISM: Artificial Sequence
<220> FEATURE:
<223> OTHER INFORMATION: Synthetic

<400> SEQUENCE: 1

Ala Ala Ala Ala Gly Gly Gly
1               5

<210> SEQ ID NO 2
<211> LENGTH: 6
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (6)..(6)
```

```
-continued

<223> OTHER INFORMATION: The residue at this position is linked to
      (COC8H16)-diacetylene-(C12H25)

<400> SEQUENCE: 2

Lys Lys Leu Leu Ala Lys
1               5

<210> SEQ ID NO 3
<211> LENGTH: 10
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (10)..(10)
<223> OTHER INFORMATION: The residue at this position is linked to
      (COC8H16)-diacetylene-(C12H25)

<400> SEQUENCE: 3

Arg Gly Asp Ser Lys Lys Leu Leu Ala Lys
1               5                   10
```

SELF-ASSEMBLING PEPTIDE AMPHIPHILES FOR TISSUE ENGINEERING

This application claims priority to provisional application Ser. No. 60/857,932, filed Nov. 9, 2006, which is herein incorporated by reference in its entirety.

FIELD OF THE INVENTION

The present invention provides for compositions and methods for creating self-assembled peptide amphiphile (PA) structures. In particular, the present invention provides for two and three-dimensional structures of crosslinked PA microtexture structures useful for tissue engineering and drug discovery.

BACKGROUND OF THE INVENTION

Significant research has been done on the effects of surface microtextures on cell behavior and how to use them to selectively stimulate cells. For example, Mata et al. (2002, Biomed. Microdev. 4:267; Mata et al., 2002, J. Biomed. Mat. Res. 62:499) describes the creation of smooth and channel micro-textures of polymethylsiloxane as substrates for growth of connective tissue progenitor cells for bone repair. Synthetic scaffolds have also been engineered to mimic the topography exhibited by extracellular matrix components for use as a potential substrate for cell growth and proliferation (Hosseinkhani et al., 2006, T. Bio. Comp. Poly. 21:277). Likewise, recent work on cell growth characteristics was performed on the surface of diacetylene peptide amphiphile hydrogels (Biesalski et al., 2006, Biomat. 27:1259). However, microtexture structures of self-assembling materials or peptide amphiphiles is not present in the literature (von Recum et al., 1996, Tissue Eng. 2:241; Curtis and Wilkinson, 1998, Biomaterials 18:1573; Xia and Whitesides, 1998, Ann. Rev. Mat. Sci. 28:153).

As such, what are needed are compositions and methods for providing tools for medicine and research, such that future work in the treatment of trauma, disease and genetic defects and drug discovery can be realized.

SUMMARY OF THE INVENTION

The present invention provides for compositions and methods for creating self-assembled peptide amphiphile (PA) structures. In particular, the present invention provides for two and three-dimensional structures of crosslinked PA microtexture structures useful for tissue engineering and drug discovery.

For example, in some embodiments, the present invention provides a polymer of a peptide amphiphile (e.g., comprising a crosslinkable or polymerizable moiety), wherein at least one surface of the polymer comprises microtexture. In some embodiments, the polymerizable moiety is a diacetylene. In some embodiments, the peptide amphiphile comprises the crosslinkable or polymerizable moiety in an alkyl tail region of the peptide amphiphile. In some embodiments, the crosslinkable or polymerizable moiety is crosslinked or polymerized in the polymer (e.g., via irradiation or other methods). In some embodiments, the microtextures comprise one or more channels and/or holes. In some embodiments, the peptide amphiphile further comprises a bioactive epitope. In some embodiments, the polymer comprises aligned nanofibers of the peptide amphiphile. Examples of microtextures useful in embodiments of the present invention include, but are not limited to, holes, posts, channels, pyramids, and any topography with reproducible geometry.

The present invention further provides a method for making peptide amphiphile microtextured structures comprising: applying peptide amphiphiles (e.g., comprising a crosslinkable or polymerizable moiety) to a mold comprising at least one surface, wherein at least one surface of the mold comprises microtextures; and crosslinking or polymerizing the peptide amphiphiles to generate a peptide amphiphile polymer comprising microtextures. In some embodiments, the crosslinking or polymerizing is achieved by irradiation. In some embodiments, prior to the crosslinking step, evaporation-based processes are applied to the peptide amphiphiles. In some embodiments, the polymerizable moiety is a diacetylene. In some embodiments, the peptide amphiphile comprises the crosslinkable or polymerizable moiety in the alkyl tail region of the peptide amphiphile. In some embodiments, the peptide amphiphile further comprises a bioactive epitope. In some embodiments, the method further comprises the step of extruding the peptide amphiphile material into the mold under conditions such that generate alignment of the peptide amphiphile nanofibers (e.g., using a pipette or other extrusion device).

The present invention additionally provides a method of affecting cellular proliferation, comprising contacting a cell with a polymer of a peptide amphiphile (e.g., comprising a crosslinkable or polymerizable moiety), wherein at least one surface of the polymer comprises microtexture, under conditions such that the cell undergoes proliferation.

The present invention also provides a method of inducing cellular differentiation, comprising contacting a stem cell with a polymer of a peptide amphiphile (e.g., comprising a crosslinkable or polymerizable moiety), wherein at least one surface of the polymer comprises microtexture under conditions such that the cell undergoes differentiation.

In other embodiments, the present invention provides methods of affecting cellular migration, comprising contacting a cell with a polymer of a peptide amphiphile (e.g., comprising a crosslinkable or polymerizable moiety), wherein at least one surface of the polymer comprises microtexture under conditions such that the cell migrates into a microtexture (e.g., hole) in the polymer.

DEFINITIONS

As used herein, the term "subject" refers to any animal (e.g., a mammal), including, but not limited to, humans, non-human primates, rodents, and the like, which is to be the recipient of a particular treatment. Typically, the terms "subject" and "patient" are used interchangeably herein in reference to a human subject.

As used herein, the term "viable cell scaffold" refers to the arrangement of the peptide amphiphiles as described herein such that cells, for example mammalian cells or tissue, can attach, grow and remain viable (e.g., survive for days, weeks, proliferate, divide, etc.) while attached to the scaffold.

As used herein, the term "sample" is used in its broadest sense. In one sense, it is meant to include a specimen or culture obtained from any source, as well as biological and environmental samples. Biological samples may be obtained from animals (including humans) and encompass fluids, solids, tissues, and gases. Biological samples include blood products, such as plasma, serum and the like. Such examples are not however to be construed as limiting the sample types applicable to the present invention.

As used herein, the term "crosslinkable moiety" refers to any moiety or compound that can be crosslinked (e.g., spontaneously or using chemical or environmental (e.g., heat or light) methods). Examples of crosslinkable moieties include, but are not limited to, coumarins, maleimide derivatives and divinylbenzenes.

As used herein, the term "polymerizable moiety" refers to any moiety or compound that can be polymerized (e.g., spontaneously or using chemical or environmental (e.g., heat or light) methods). Examples of polymerizable moieties include, but are not limited to, diacetylene.

DETAILED DESCRIPTION OF THE INVENTION

The compositions and methods described herein provide microstructures made from peptide amphiphiles (PA) that self-assemble while conforming to molds with micro or nano-scale resolution. The technique described herein is useful for the creation of tissue engineering viable cell scaffolds that provide a two (2D) or three dimensional (3D) space with both selective biochemical signaling and precise physical control. The scaffolds of the present invention provide control, and stimulate cell behavior and subsequent tissue genesis, by providing precise geometric and biochemical control of biological processes from the molecular to the tissue level.

I. Peptide Amphiphiles

Self-assembly of PAs by β-sheet formation of the peptide segments and hydrophobic collapse of the aliphatic chains results in one-dimensional nanofibers or networks thereof to give gels in certain conditions. This PA nanofiber system has shown potential for various applications including regenerative medicine (Silva et al., 2004, Science 303:1352), tissue engineering (Beniash et al., 2005, Acta Bio. 1:387) or chemotherapy (Bull et al., 2005, Nano Lett. 5:1) based on the epitopes displayed on the periphery. However, the PA gels created to date are weak in nature, and therefore very difficult to use as substrates for tissue growth and regeneration in vivo.

Self-assembly of PAs can be controlled by pH, electrostatic interaction, and addition of multivalent ions, causing the ionic character of certain amino acid side chains to be screened so that PAs can effectively interact with each other through hydrogen bonding and induced hydrophobic collapse (Hartgerink et al., 2002; Hartgerink et al., 2001; Niece et al., 2003, J. Am. Chem. Soc. 125:7146; Stendahl et al., 2006, Adv. Func. Mat. 16:499). Specifically, one class of PA systems that was designed to form nanofibers under acidic conditions is comprised of palmitic acid covalently linked to a β-sheet forming peptide sequence such as AAAAGGG (SEQ ID NO. 1), followed by a negatively charged peptide sequence such as FEE.

In some embodiments, the present invention provides that a crosslinking or polymerizable group added to a self-assembled system enhances the overall rigidity of an entire supramolecular structure, resulting in the formation of a more robust material. The PAs of the present invention self-assemble into micro-long nanofibers, driven primarily by hydrophobic forces and β-sheet formation. In some embodiments, an additional modification to these peptide amphiphiles is made, thereby enabling crosslinking functionality while still maintaining the monomer's ability to self-assemble into nanofibers. For example, the addition of a unsaturated hydrocarbon diacetylene ($C_4H_2$, also known as butadiyne and buta-1,3-diyne) crosslinker into the alkyl tail region of the monomer exhibits polymerization along the z-axis of the fiber.

Crosslinking a self-assembled supramolecular structure while maintaining the self-assembled PA structure creates stiffer self-supporting PA hydrogels. In comparison to non-polymerized PAs that form weak gels that cannot withstand physical manipulation, the polymerized crosslinked PAs can physically be manipulated without breaking the hydrogel form. The present invention is not limited to a particular crosslinker or polymerizable moiety. Other crosslinkable moieties, including coumarins and maleimide derivatives which embody similar topotactic chemistry may be used. In other embodiments, divinylbenzenes (e.g., Angew Chem Int Ed Engl. 2007; 46(26):4987-90) are used as crosslinking agents.

In some embodiments, the present invention provides PA molecules containing diacetylene molecules with a β-sheet forming region that are able to self-assemble into high aspect-ratio nanofibers. In contrast, prior molecules were synthesized for either monolayer or LB-film studies (Nezu and Lando, 1995, 33:2455; Biesalski et al, 2005, Langmuir 21:5663; Lee et al., 2005, Nano Lett. 5:2202; Jahnke et al., 2006, Angew. Chem. 45:5383; Biesalski et al, 2006, Biomaterials 27:1259). More recent applications use the prior molecules to form crosslinked micellular nanospheres as potential biosensors or drug delivery vehicles, however none of the micellular nanopheres have proven useful to date.

The structure of a PA molecule can be divided into three major segments: i) the bioactive hydrophilic section, ii) the β-sheet forming region, and iii) the hydrophobic alkyl tail region. Self-assembly of these molecules are controlled by pH, temperature, or cation selection, depending on the peptidic sequence. Under aqueous conditions, the alkyl tails bury themselves within the interior of the fiber core, exposing the bioactive, hydrophilic segment. The morphology of the nanofiber is due to the β-sheet formation, which runs along the z-axis of the fiber. Once self-assembled, these molecules form long nanofibers which can overlap with other nanofibers to form large three-dimensional networks.

On the macroscale, the observed solution becomes a self-supporting hydrogel. The distinct regions of the PA can be tailored to accommodate various bioactive epitope sequences, while still maintaining self-assembling capabilities for hydrogel formation. The present invention is not limited by the bioactive epitope used, and any epitope that allows for the formation of three-dimensional long nanofibers as described herein may be used.

Current peptide amphiphiles have the mechanical consistency of a very weak hydrogel that cannot withstand significant external stress. Some embodiments of the present invention provide for inclusion of a diacetylene group within the core of the alkyl tail region that serves to crosslink the nanofibers, resulting in the formation of more robust PA hydrogels. In some embodiments, crosslinking or polymerizing of the nanofibers is performed by irradiation at <300 nm for several minutes, resulting in the expected colorimetric change from a colorless gel to a bluish gel. The nanofibers also form in solution at very low concentrations, as observed by a color change after UV irradiation. No chemical degradation of the peptide molecules is observed upon UV irradiation and overall nanofiber morphology is maintained.

In one embodiment, crosslinked nanofibers of diacetylene PAs are formed by irradiation with ultraviolet light at <300 nm for at least 1, at least 2, at least 3, at least 4 minutes. In some embodiments, the crosslinked nanofibers of diacetylene PAs form hydrogels able to withstand mechanical stress to a greater extent than hydrogels formed without diacetylene.

In other embodiments, additional diacetylene contained molecules are utilized to form polymers. Examples include, but are not limited to, 5,7-docosadiynoic acid, 5,7-pentacosadiynoic acid, and 10,12-pentacosadiynoic acid (See e.g., U.S. Pat. No. 6,306,598; herein incorporated by reference).

Figure 12:
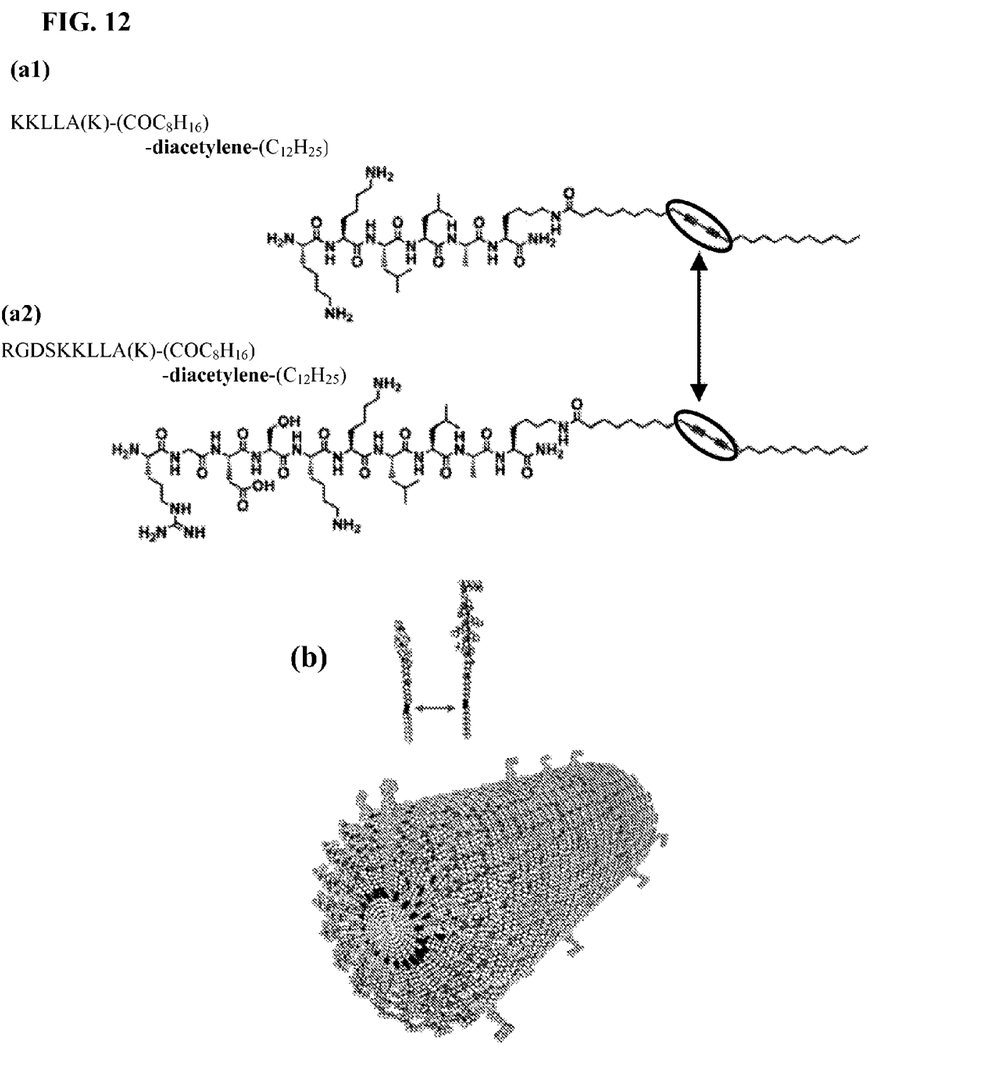
FIG. 12 show a schematic of crosslinked PA nanofibers.

FIG. 12 shows an exemplary PA and nanofiber that finds use in some embodiments described herein. FIG. 12 illustrates the molecular structure of two individual PA molecules (a) and the corresponding self-assembled nanofiber (b). The molecular structure of both individual peptide amphiphile molecules comprises a photo-crosslinkable diacetylene segment in the hydrophobic alkyl tail of the PA to promote intra fiber crosslinks. The first PA molecule (a1) does not contain a bioactive epitope and serves as a filler to space out the bioactive PA molecule (a2), which has the amino acid sequence arginine-glycine-aspartic acid (RGD) for integrin-based recognition and subsequent improved cell adhesion (a2). (b) Illustration of the self-assembled nanofiber consisting of ~10% of the RGD-containing PA (a2) and ~90% of the filler PA (a1).

Each PA molecule comprises a diacetylene segment on the hydrophobic alkyl tail. Self-assembly of the PA molecules results from hydrophobic collapse of the aliphatic tails and β-sheet formations, which results in well defined nanofibers of about 8 nm in diameter and microns in length with the hydrophilic bioactive segment exposed at its surface. At this point, the PA nanofibers (made from assembled PA molecules) are exposed to UV light (265 nm wavelength), which leads to a polymerization reaction that results in a polydiacetylene backbone within the nanofiber.

Other PAs suitable for use in the present invention include, but are not limited to, V3A3E3 and the V3A3K3 PA in combination with hyaluronic acid. With the V3A3E3 PA, the same protocol for generation of polymers as described herein is followed except that an acid chamber is used instead of a basic one. With the V3A3K3 PA+hyaluronic acid, the protocol described herein is followed except that once the stamping is done, there is no need for an acid or basic chamber, simply time at room temperature.

II. Generation of Microtextures

In some embodiments, the present invention provides for methods for the creation of self-assembling PA multidimensional microtextures for tissue engineering, drug discovery, production, or other applications. In some embodiments, PA microtexture structures are created using a mold. In some embodiments, the PA microtexture structures are created using an evaporation-based process. In some embodiments, the PA structures comprise channels, whereas in other embodiments the PA structures comprise holes. In some embodiments, the PA microtexture structures are created by crosslinking the PA gel upon application of ultraviolet radiation. In some embodiments, the ultraviolet radiation used to crosslink the PA gel is <300 nm. In some embodiments, the molds used to create the PA microtexture structures comprise silica and polydimethylsiloxane. The present invention is not limited by the composition of the molds used, and skilled artisans will recognize alternatives that are equally applicable for the creation of the PA microtexture structures.

The compositions and methods of the present invention involve, for example, evaporation to gradually and uniformly lay and stack self-assembled PA nanofibers on a mold that can be removed while keeping the molded structures. The resultant microstructures are made (completed or in part) of PA materials. The methods for PA microtexturing as described herein allow for the creation of highly biocompatible substrates that can further combine specific biochemical (through bioactive epitopes) and physical (through surface topography) stimuli for the control of cell behavior. Current lithographic techniques to create thin layers comprising precise microstructures include nanoimprint lithography (NIL), step-and-flash imprint lithography (SFIL), replica molding (RM) and solvent assisted micro-molding (SAMIM).

The present invention provides methods to generate precise 2D or 3D micro/nano structures of self-assembled PAs. The methods permit the use of micro-fluidic principles to align the self-assembled nanostructures, while at the same time conforming them on any desired 3D micro-structure. The thickness and properties of the resultant film are controlled by the concentration of the material in the solvent, the evaporation conditions (e.g., time, pressure, temperature, pH), and the applied force between the molds.

Figure 1:
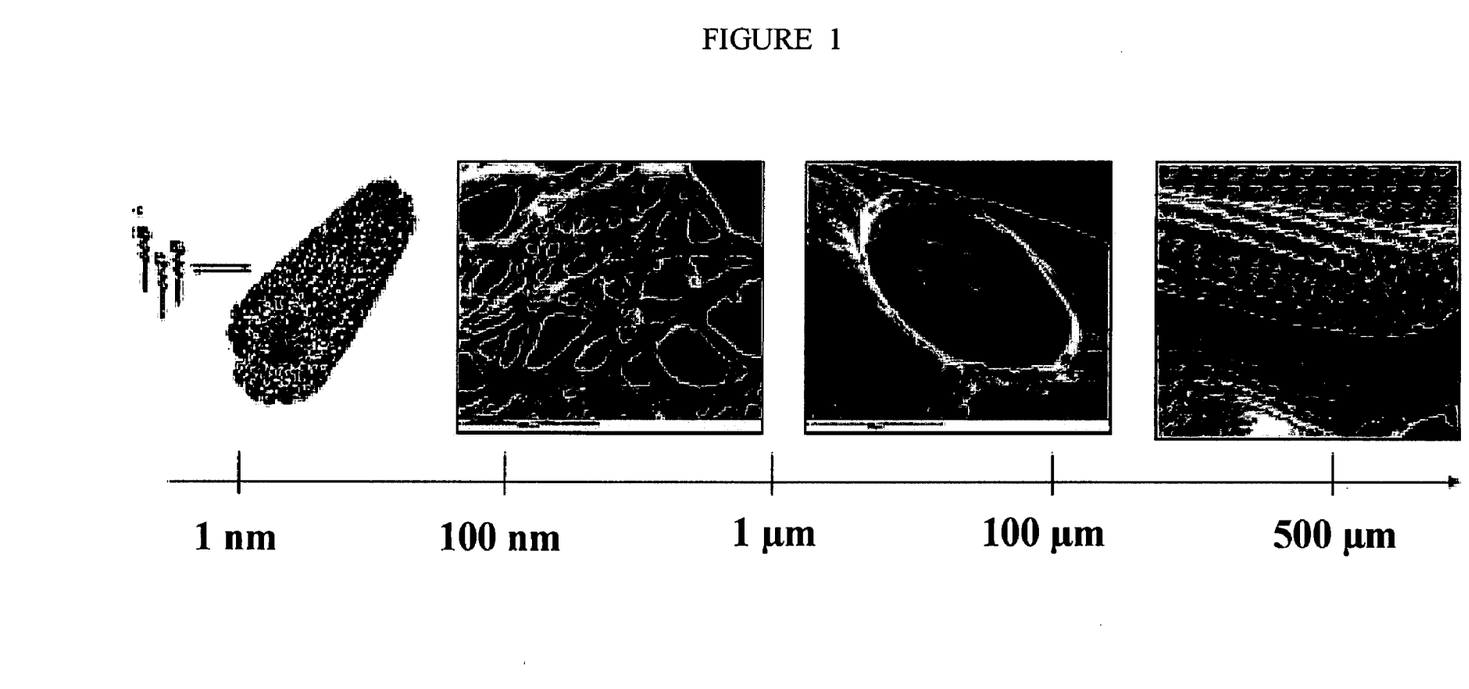
FIG. 1 illustrates the formation of specific microtextures with defined geometric features made from self-assembled bioactive nanofibers. The structures are useful to fabricate biomimetic environments with multidimensional resolution.

The methods of embodiments of the present invention allow for the geometric control of self-assembling peptide amphiphiles into well-defined nanofibers, and further, into well defined surface microtextures (FIG. 1). The resultant microtexture substrates achieve geometrical control of biological events through biochemical and physical stimuli within a multidimensional environment.

Figure 2:
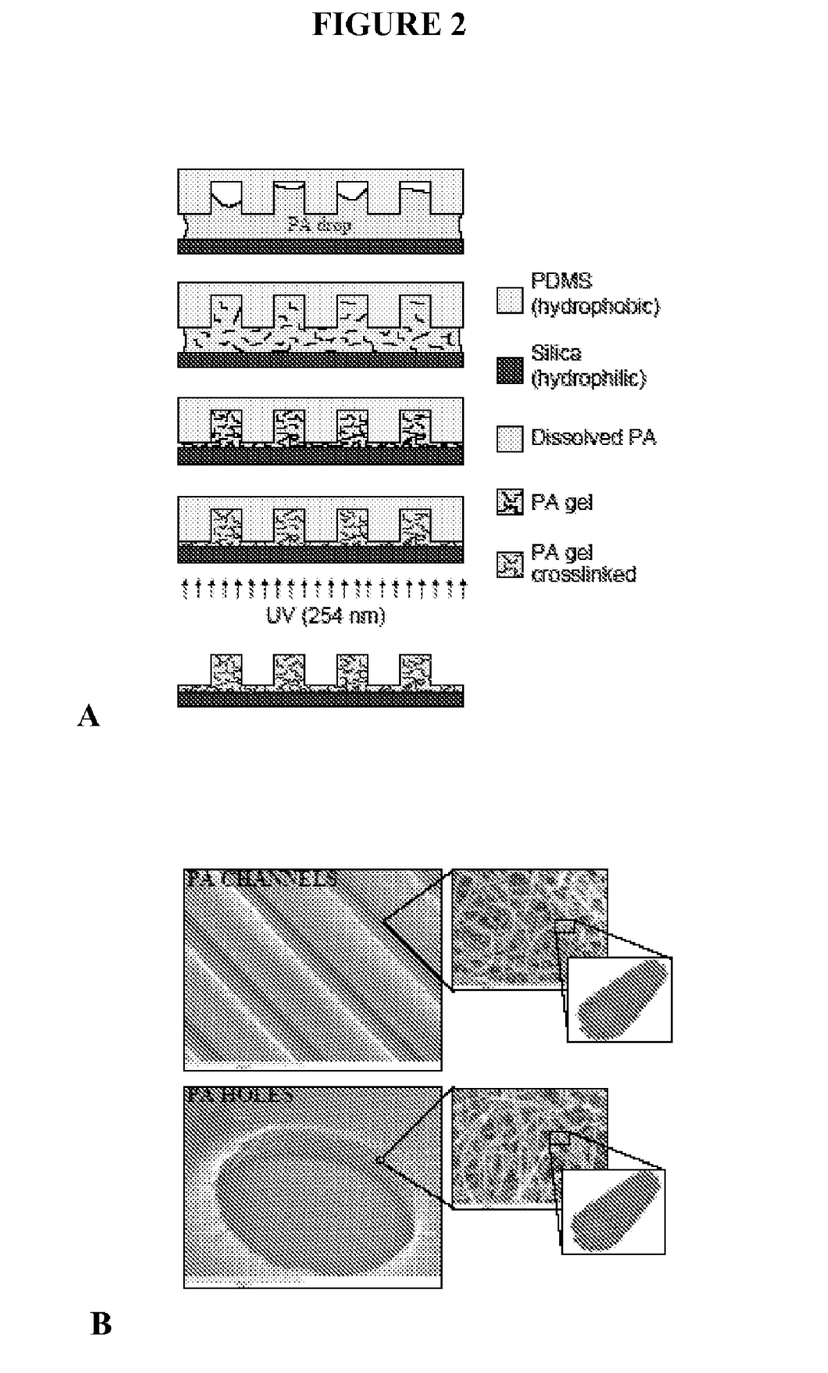
FIG. 2 depicts a process for microtexturing (A) of the PA matrices, and the corresponding PA microtexturing product as seen by electron microscopy (B). PDMS=polydimethylsiloxane.
Figure 3:
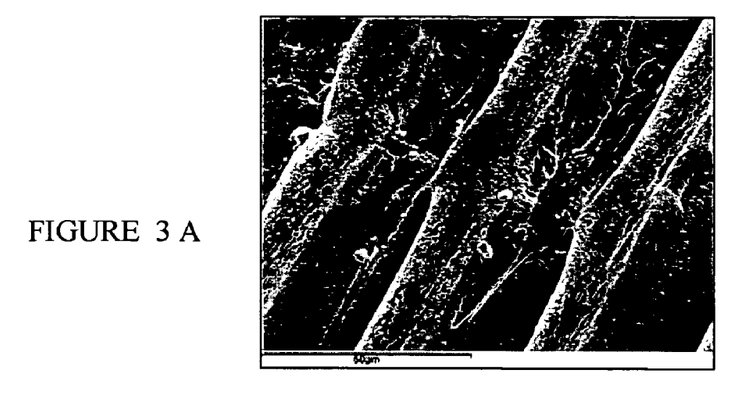
FIG. 3 shows the growth of cells on the PA matrices of the present invention (A) PA channels and (B) PA holes.

In some embodiments, dissolved PA material as described herein is positioned between two molds, which can have microtextures or smooth surfaces (FIG. 2A). The PA is self-assembled while evaporation takes place and increases the concentration of the PA material. Ultraviolet irradiation (<300 nm, preferably about 254 nm) is used to cross-link the diacetylene molecules present in the core of the nanofibers and increase the overall gel strength. The molds are separated and the PA microtextures are released (FIG. 2A), resulting in channels or holes (FIG. 2B). The PA microtextures comprising specific biochemical stimuli (provided by the nanofibers)

and selective physical stimuli (provided by the precise geometrical features) can then be used to selectively manipulate cells (FIGS. 3A&B).

In some embodiments, nanofibers of PA material are aligned by depositing on substrates in a control (e.g., linear) manner. For example, in some embodiments, pipettes or other extrusion devices are used to extrude the PA material into the mold in a linear manner. This allows one to control the way in which the bioactive epitopes are presented from the molecular, to the nano, to the micro, all the way to the macro level.

III. Uses of PA Microstructures

In some embodiments, the compositions and methods described herein provide substrates for cellular growth and differentiation. Experiments conducted during the development of embodiments of the present invention demonstrated that substrates comprising microtextures increased cellular proliferation, differentiation, and induced migration into specific portions of the microstructures.

The compositions and methods of the present application find utility in commercial applications, including but not limited to, bioreactors made with (2D) two-dimensional or 3D microfabricated PA substrates for selective cell (e.g., stem cell) control and growth. Expanded cell populations, like those created in a bioreactor, are implanted into patients suffering from, for example, trauma, disease or genetic defect.

The compositions of the present invention also serve as substrates for multidimensional cell control and environments for the screening of cellular reactions to different chemicals or medications, thereby allowing for drug discovery and additional biosensing applications.

For example, in one embodiment, the PA microtexture structures as described herein provide a method for drug discovery. In some embodiments, the PA microtexture structures are used to grow cells of use in screening drugs, compounds or small molecules for drug discovery. In some embodiments, cells useful for drug discovery grown on the PA microtexture structures include, but are not limited to, fibroblasts, cancer stem cells, or immortalized tissue culture cells (e.g., HeLa, CHO, 293, BALB 3T3, etc.). In some embodiments, cells are grown on the PA microtexture structures and drugs, compounds, or small molecules are applied to the cells to access the efficacy of the drug, compound, or small molecule as an antagonist or agonist of cell growth. In some embodiments, the PA microtexture structures as described herein are used in biosensing applications.

In other embodiments, the PA microtextures are used as a nucleating surface for growth of crystals (e.g., for protein or chemical structure and function analysis).

EXPERIMENTAL

The following examples are provided in order to demonstrate and further illustrate certain preferred embodiments and aspects of the present invention and are not to be construed as limiting the scope thereof.

Example 1

Use of PA Microtextures

1. Effect on Cell Differentiation

Figure 4:
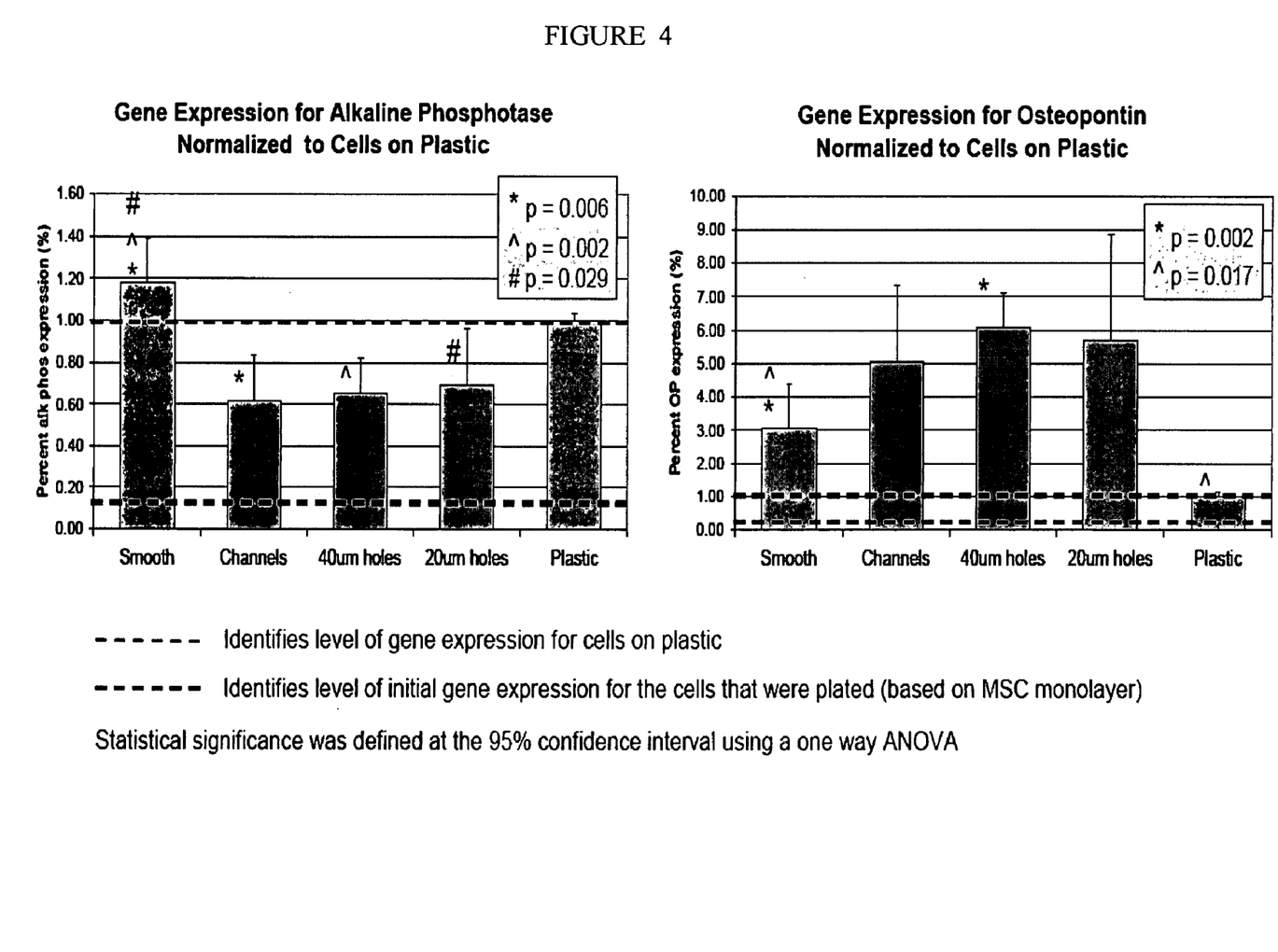
FIG. 4 shows gene expression for alkaline phosphatase (left) and Osteopontin (right) for stem cells cultured on crosslinked PA polymers of some embodiments of the present invention.

PA microtextures were used to promote osteoblastic differentiation. The PA materials used in these experiments comprise the bioactive epitope RGD for cell adhesion. Three different PA microtextures were fabricated and tested. In addition, two different substrates were used to serve as controls to take into account material differences and microtexture (topographic) differences. The experiment was repeated 4-6 times. The tested substrates were:

40 μm Holes: PA microtextures with 40 μm diameter, 5-10 μm high holes
20 μm Holes: PA microtextures with 20 μm diameter, 5-10 μm high holes
Channels: PA microtextures with 20 μm wide channels, 5-10 μm high channels
Smooth: Smooth (no microtextures) PA material. Control for topography effect
Tissue Culture Polystyrene (Plastic): Smooth (no microtextures) polystyrene material.
Control for Material Effect These samples served as substrates for in vitro culturing of Human Mesenchymal Stem Cells (hMSCs). At Day 7, the cells were fixed and analyzed using RT-PCR for gene expression of osteoblastic markers including Alkaline Phosphotase (ALP) and Osteopontin (OP). The results are presented in FIG. 4 and illustrate a significant increase of osteoblastic phenotype on the cells growing on the PA microtextures. From the graph on the left of FIG. 4, it can be seen that at Day 7 the cells on the PA microtextures have lower gene expression for ALP (which is an earlier osteoblastic marker) but as observed from the graph on the right of FIG. 4 these cells have a significantly higher expression of OP (which is a later, more mature osteoblastic marker). The cells on PA microtextures differentiated faster into an osteoblastic phenotype compared to cells on Smooth and Plastic, moving faster from ALP production into OP production. This effect is highest on cells growing on 40 μm holes, which exhibit a statistically significant difference.

Figure 11:
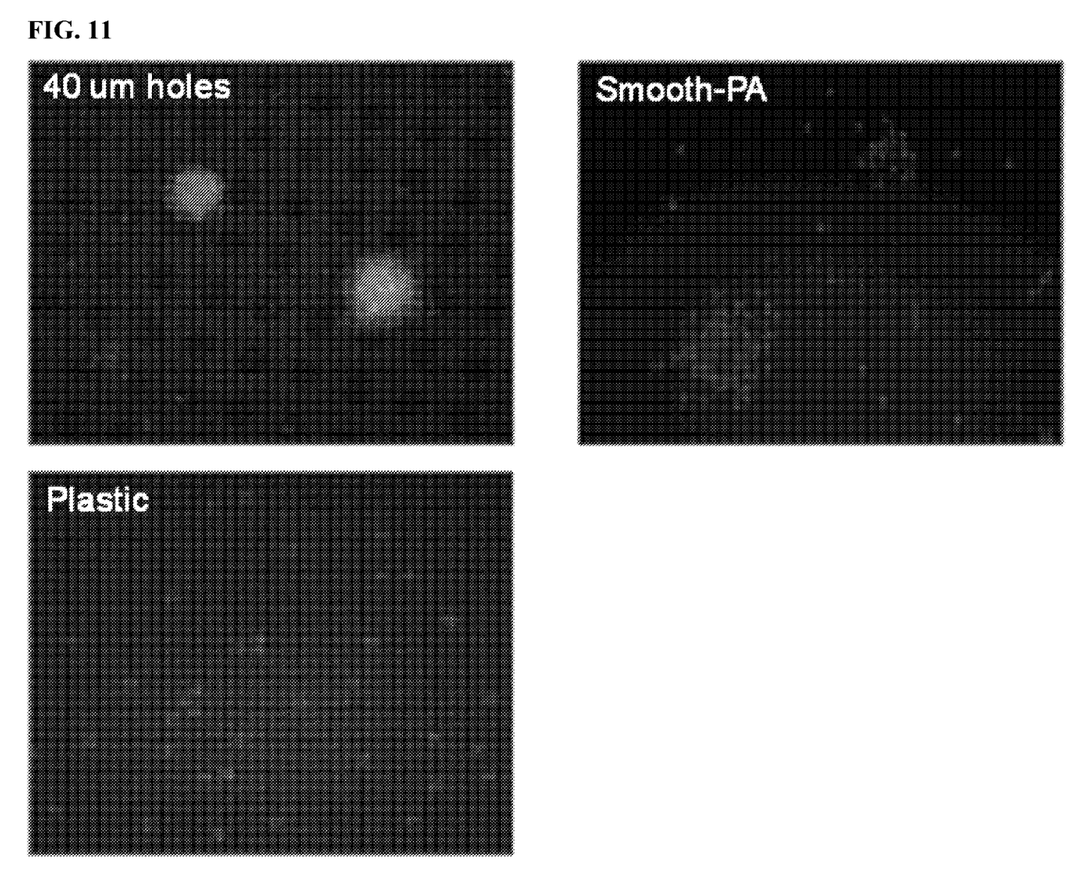
FIG. 11 shows staining of Core Binding Factor α-1 (CBFa-1) grown on exemplary microtextures of embodiments of the present invention.

In order to confirm this data Core Binding Factor α-1 (CBFa-1) was stained, which is a critical transcription factor for osteoblastic differentiation. Cells growing on the 40 μm holes, smooth PA substrates, and tissue culture plastic were stained at day 7. Groups of cells growing on 40 μm holes were the only cells that were observed to stain (green) for the CBFa-1, confirming the increased differentiated state evident in the previous RT-PCR experiments (FIG. 11). In addition, cells on the 40 μm holes formed nodule-like structures, which have been linked to osteoblastic differentiation of HMSCs.

2. Effect on Cell Adhesion and Proliferation

Figure 5:
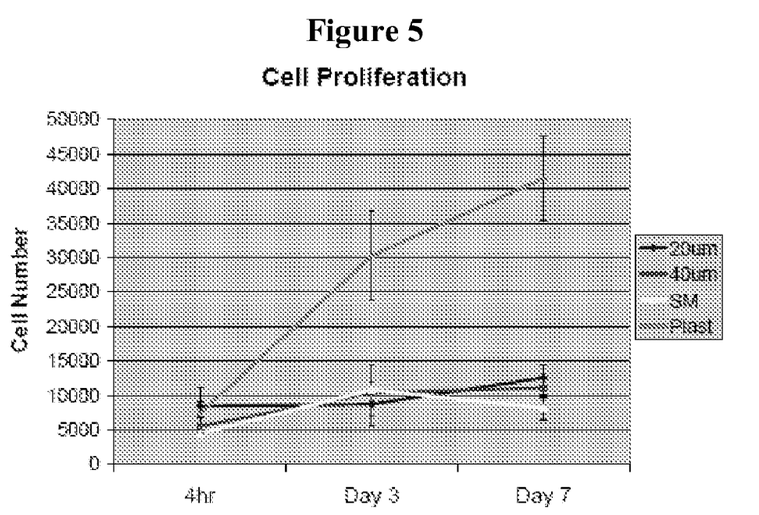
FIG. 5 shows cellular proliferation of cells cultured on crosslinked PA polymers of some embodiments of the present invention.
Figure 6:
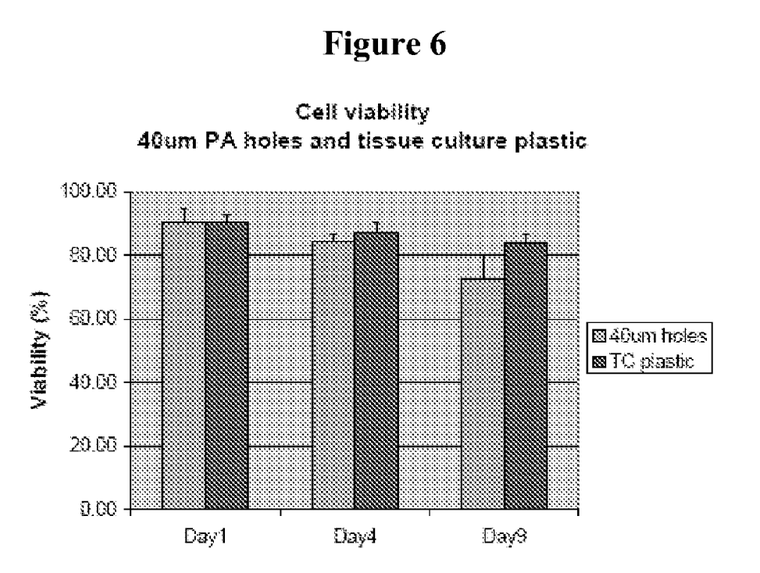
FIG. 6 shows cell viability of cells cultured on crosslinked PA polymers of some embodiments of the present invention.

In addition to osteoblastic differentiation, cell adhesion and proliferation were quantified. There was no significant difference in initial adhesion of cells to their substrates between all the PA microtextures and the tissue culture plastic (Plastic) (FIG. 5, below left). However, cell proliferation was significantly higher on cells growing on Plastic compared to PA microtextures. Cell number on PA microtextures was relatively constant throughout the 7 day culture. In order to test the possibility of similar proliferation rate (between cells on Plastic and PA microtextures) but higher cell death on PA microtextures, a live/dead assay was conducted. Cells on both Plastic and 40 μm holes exhibited a slight decrease in viability, which has been previously observed when cells are grown in osteogenic media. Viability is defined as the percent of live cells with respect to the total (live+dead) cells. At Day 9, the viability of cells on Plastic was 84%, while those on 40 μm holes was 72% (FIG. 6). Although there was a 12% decrease in viability, this difference is too small to account for the large proliferation difference between cells on Plastic and those on 40 μm holes. The present invention is not limited to a particular mechanism. Indeed, an understanding of the mechanism is not necessary to practice the present invention. Nonetheless, it is contemplated that the low proliferation of cells on PA microtextures is due to a more mature differentiation stage, which is supported by the higher expression of Osteopontin and staining for CBFa-1.

3. Effect on Cell Morphology

Figure 7:
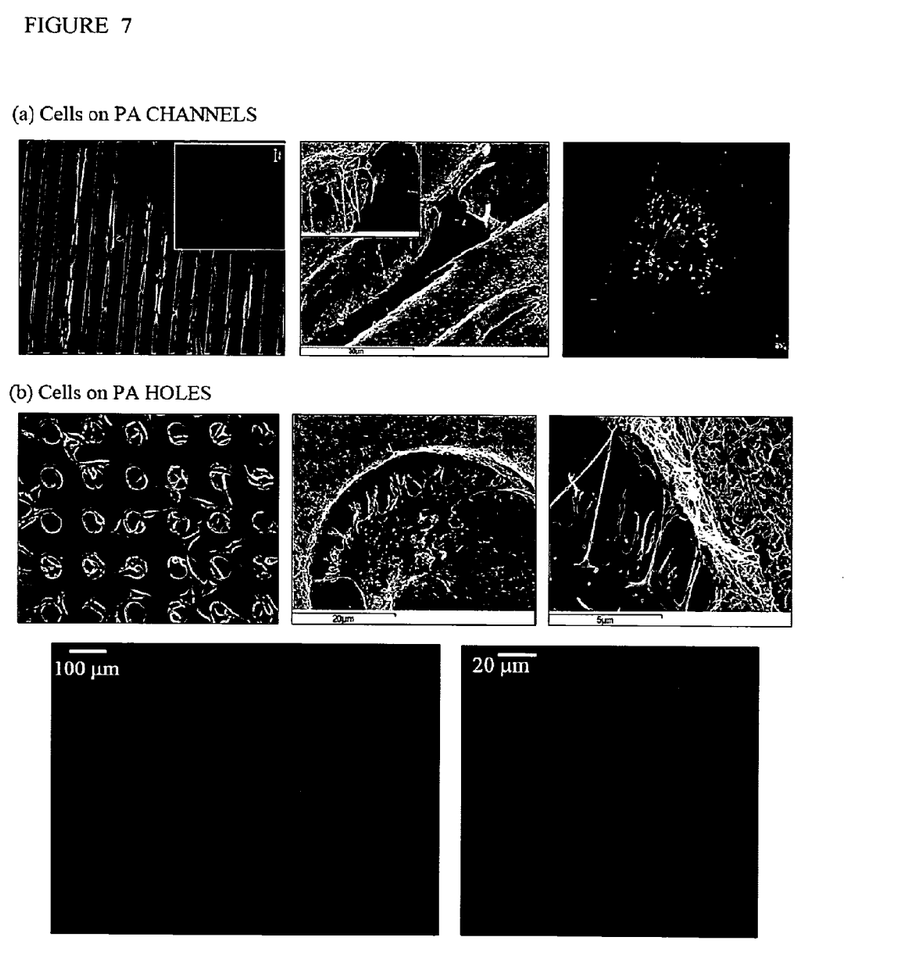
FIG. 7 shows cellular morphology of cells cultured on crosslinked PA polymers of some embodiments of the present invention. Immunofluorescent staining depicts the effect of PA microtexture on the overall cellular morphology as observed by actin cytoskeleton, cell nuclei, and focal adhesions.

Cells on the PA channels aligned along the channel direction and expressed actin and focal adhesion alignment (FIG. 7, below (a)). Moreover, cells migrated along the channel direction while interacting with the horizontal and vertical walls of the channels. Cells on PA holes were confined within the holes and seemed to preferentially interact with the PA nanofibers present on the 10 μm high vertical walls (FIG. 7, below (b)). Actin cytoskeleton and nuclei of the cells was observed to be present inside the 40 μm holes.

4. Effect on Cell Migration

Figure 8:
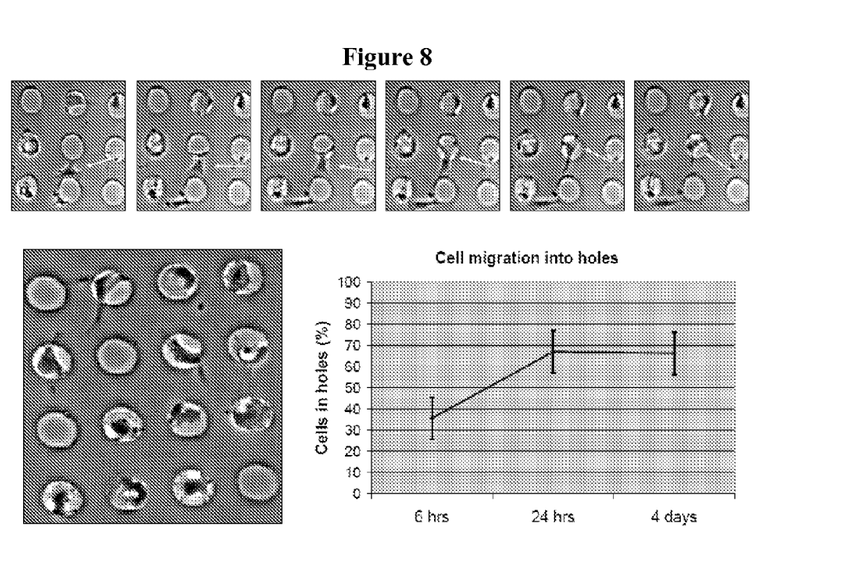
FIG. 8 shows cellular migration of cells cultured on crosslinked PA polymers of some embodiments of the present invention.

Cells on PA HOLES were often observed to recognize the edge of the holes and migrate inside the 40 μm holes as was evident by time-lapse microscopy. In contrast, cells on similar microtextures but that were made from polydimethysiloxane (PDMS) did not exhibit this kind of migration. This behavior shows that cells are recognizing both the RGD epitopes from the nanofibers and the topographical features from the 40 μm holes. The images (FIG. 8) illustrate a cell (white arrow) recognizing the edge of a hole and migrating inside of the hole while interacting with the edge. The migration of the cells inside the 40 μm holes was observed to occur primarily within the first 24 hrs after inoculation. Six hours after inoculation about 35% of the cells were located inside of the holes followed by 67% of all cells migrating within the holes just 18 hrs after that. This number was constant at least during the next 3 days. This preference of HMSCs for growing within the 40 μm holes and interacting with the vertical walls of the holes shows that is directly related to the increased osteoblastic differentiation observed on cells growing on these microtextures (compared to cells on smooth PA and Plastic).

Example 2

Fabrication of Microtextures

1. Fabrication of PA Microtextures with Aligned Nanofibers

Figure 9:
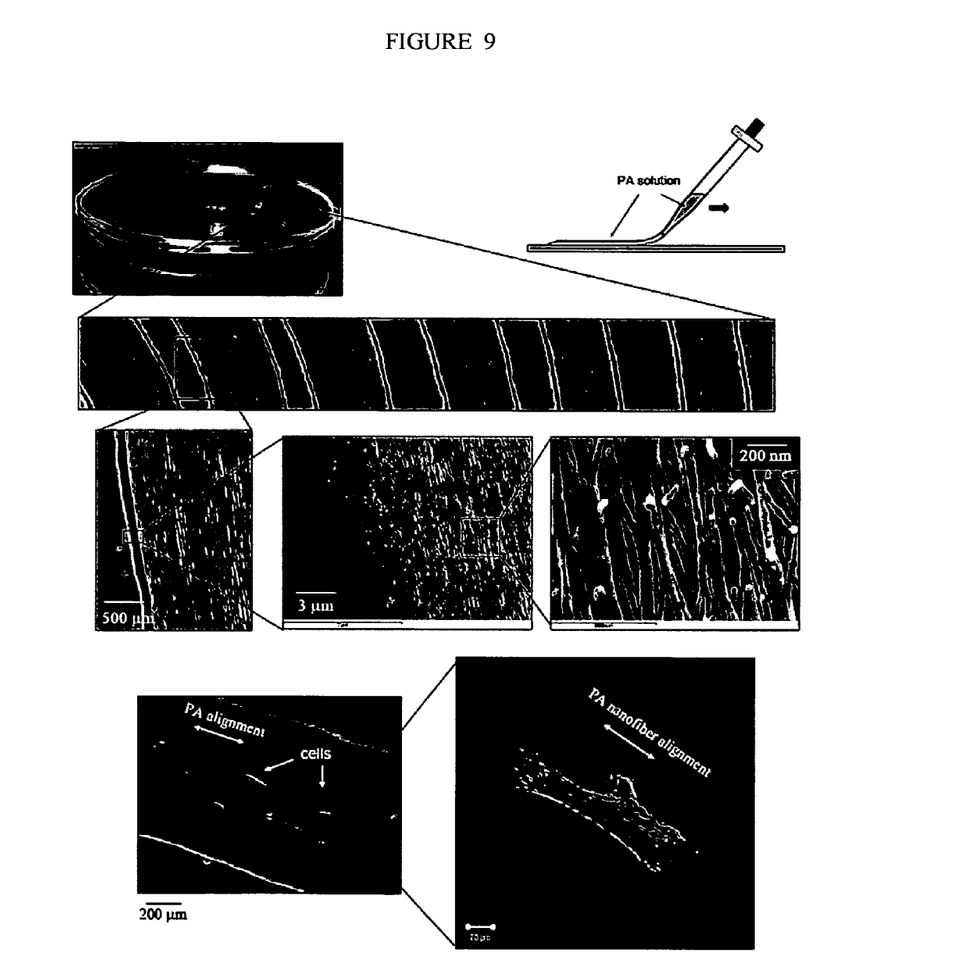
FIG. 9 shows method of fabricating microtextured polymers comprising aligned nanofibers and the corresponding cellular recognition of this nanofiber alignment.

An additional fabrication process was utilized that used a pipette to extrude the PA material, which is then textured in the same way as described above. This is done in order to further increase the topographical control of these PA microstructures by aligning the PA nanofibers, and increase the overall control over the presentation of the bioactive epitopes. In this way, it was possible to control not only the nano- and micro-topographical features that interact with the cells but also control the way in which the bioactive epitopes are presented from the molecular, to the nano, to the micro, all the way to the macro level. The developed PA microtextures comprised aligned PA nanofibers which offer a high level of topographical and epitope presentation control (FIG. 9 below).

2. Effect of PA Nanofiber Alignment and PA Microtextures on HMSC Alignment

Figure 10:
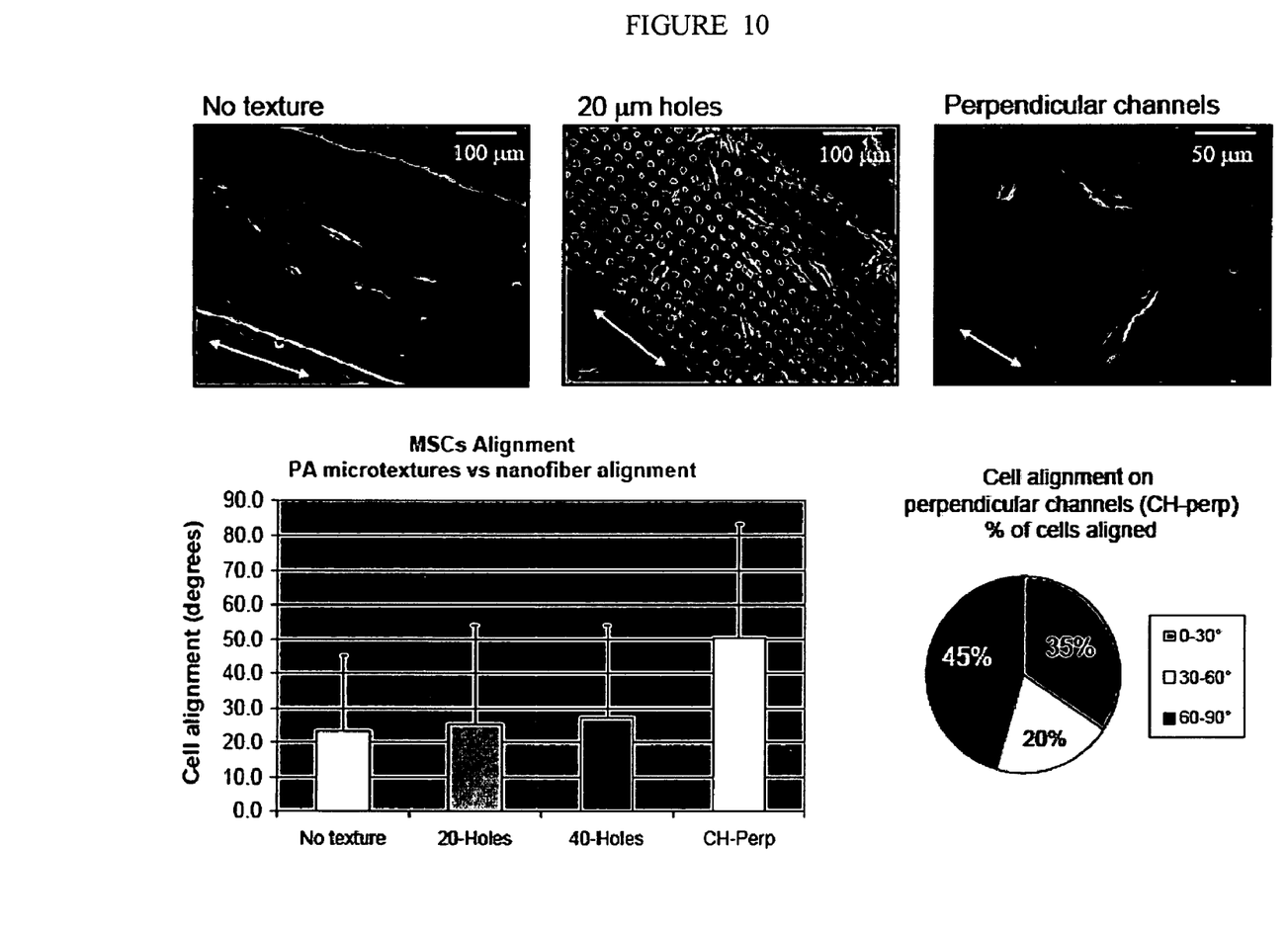
FIG. 10 shows cell alignment on microtextured polymers comprising aligned nanofibers.

Using similar casting techniques to those used for the development of substrates for osteoblast differentiation, microtextures were fabricated using the PA spiral patterns. MSCs were cultured on these aligned nanofiber structures with either 20 μm holes, 40 μm holes, or 20 μm channels and individual cell alignment was quantified. Cells aligned along the nanofiber direction on the substrate without microtexture (only aligned PA nanofibers), the 20 μm holes and the 40 μm holes. However, on the micro-channels that were perpendicular to the direction of the nanofibers, the cells were either aligned to the nanofibers or to the micro-channels. 45% of all cells aligned to the micro-channels, while 35% of all cells aligned to the nanofibers instead (FIG. 10).

Examples 1 and 2 demonstrate the utilization of microfabrication and soft lithographic techniques to create precise surface micro-textures made from self-assembling peptide amphiphiles (PAs). PA micro-textures provided cell adhesion epitopes for cell recognition as well as three-dimensional structures for contact guidance and cell growth manipulation. Bioactive substrates with both molecularly designed bioactive surface microtextures are provided for control and manipulation of stem cells into the osteogenic phenotype.

We claim:

1. A microtextured structure comprising a crosslinked or polymerized peptide amphiphile, wherein said peptide amphiphile comprises a crosslinkable or polymerizable diacetylene moiety, and wherein at least one surface of said microtextured structure comprises mold-formed channels or holes, wherein said mold-formed channels or holes are 5-10 μm in depth.

2. The microtextured structure of claim 1, wherein said microtextured structure comprises mold-formed channels.

3. The microtextured structure of claim 1, wherein said peptide amphiphile comprises said crosslinkable moiety in an alkyl tail region of said peptide amphiphile.

4. The microtextured structure of claim 1, wherein said microtextured structure comprises mold-formed holes.

5. The microtextured structure of claim 1, wherein said peptide amphiphile further comprises a bioactive epitope.

6. The microtextured structure of claim 1, wherein said polymer comprises aligned nanofibers of said peptide amphiphile.

7. The microtextured structure of claim 1, wherein said mold-formed channels or holes are 20-40 μm in width.

8. A microtextured structure comprising a crosslinked or polymerized peptide amphiphile, wherein said peptide amphiphile comprises a crosslinkable or polymerizable diacetylene moiety, and wherein at least one surface of said microtextured structure comprises mold-formed channels or holes, wherein said mold-formed channels or holes are 20-40 μm in width.

9. The microtextured structure of claim 8, wherein said microtextured structure comprises mold-formed channels.

10. The microtextured structure of claim 8, wherein said peptide amphiphile comprises said crosslinkable moiety in an alkyl tail region of said peptide amphiphile.

11. The microtextured structure of claim 8, wherein said microtextured structure comprises mold-formed holes.

12. The microtextured structure of claim 8, wherein said peptide amphiphile further comprises a bioactive epitope.

13. The microtextured structure of claim 8, wherein said polymer comprises aligned nanofibers of said peptide amphiphile.

* * * * *